(12) United States Patent
Dunleavy et al.

(10) Patent No.: US 9,539,144 B2
(45) Date of Patent: Jan. 10, 2017

(54) GOGGLE ACCESSORY

(75) Inventors: Bonnie Marie Dunleavy, Galway, NY (US); Jennifer L. Bailey, Queensbury, NY (US); Kimberly Jane Moore, Scotia, NY (US)

(73) Assignee: Z Tuck, LLC, Galway, NY (US)

( * ) Notice: Subject to any disclaimer, the term of this patent is extended or adjusted under 35 U.S.C. 154(b) by 436 days.

(21) Appl. No.: 13/374,668

(22) Filed: Jan. 5, 2012

(65) Prior Publication Data

US 2012/0167277 A1 Jul. 5, 2012

Related U.S. Application Data

(60) Provisional application No. 61/430,059, filed on Jan. 5, 2011.

(51) Int. Cl.
*A61F 9/02* (2006.01)
*A42B 3/18* (2006.01)

(52) U.S. Cl.
CPC ............... *A61F 9/029* (2013.01); *A42B 3/185* (2013.01)

(58) Field of Classification Search
CPC ................................. A42B 3/185; A61F 9/029
USPC ........ 2/181.4, 243.1, 244, 209.13, 426, 438, 2/454, 452; 206/5
See application file for complete search history.

(56) References Cited

U.S. PATENT DOCUMENTS

| | | | | |
|---|---|---|---|---|
| 1,555,928 | A * | 10/1925 | Morrissey | H04R 5/0335 2/209 |
| 5,032,019 | A * | 7/1991 | Burchett | 351/158 |
| 5,428,844 | A * | 7/1995 | Dougherty | 2/209.13 |
| 5,526,924 | A * | 6/1996 | Klutznick | 206/5 |
| 6,038,706 | A * | 3/2000 | Seiler | 2/426 |
| 7,131,148 | B1 * | 11/2006 | Traumer | 2/426 |
| D628,230 | S | 11/2010 | Tobey | |
| 8,272,076 | B2 * | 9/2012 | Tobey | 2/452 |
| 2011/0252547 | A1 * | 10/2011 | Leung et al. | 2/425 |

* cited by examiner

*Primary Examiner* — Katherine Moran
(74) *Attorney, Agent, or Firm* — Genius Patent APC; Bruce Hare (57) ABSTRACT

A goggle accessory that includes a substantially planar element that has one or more folding elements along its longitudinal axis, so as to divide the planar element into multiple substantially planar sections; an attachment means configured to attach these planar sections to each other; and openings through the planar element configured to receive a goggle keeper-strap of a helmet. Other embodiments include a planar element made of a flexible material; an opening defined by the attachment of the accessory to a goggle strap; and/or design element(s) attached or integrated to the accessory. The goggle accessory offers an aesthetic design for use over a goggle strap with or without the use of a helmet and its concomitant goggle-keeper strap.

6 Claims, 6 Drawing Sheets

GOGGLE ACCESSORY

CROSS-REFERENCE TO RELATED APPLICATIONS

This application claims priority to, U.S. Patent Application Ser. No. 61/430,059, filed Jan. 5, 2011, the contents of which are hereby incorporated by reference in their entirety.

BACKGROUND OF THE INVENTION

The present invention relates generally to eye goggles and/or eyeglass wear, and more specifically, to a goggle accessory.

Eye goggles and eyeglass wear are often used in athletic and action activities. In such endeavors, eye goggles, and eyeglass wear, often include a goggle strap to aid in keeping the goggles or eyeglass wear attached to the user's head. As viewed from the back of the user, this goggle strap is in apparent view. Many goggle straps have designs, logos, words, and/or artwork incorporated thereon.

In a subset of these activities (typically, more action-oriented activities), the user concomitantly wears a protective helmet along with the eye goggles. Examples of such activities include snow sports (alpine skiing, snowboarding, etc.), many motor sports (e.g., auto racing, motorcycle racing, etc.), and even equestrian sports. Many protective helmets use a goggle keeper-strap on the back of the helmet that is configured to keep the goggle strap from riding upwards or downwards on the back of the helmet which results in the eye-covering portion of the goggles to become displaced from the user's face.

As with many athletic and action activities, accessorizing and/or customizing the user's equipment and outerwear is an omnipresent and continual opportunity. Accordingly, there is an ongoing opportunity for improving upon the use of eye goggles and their accessories.

BRIEF DESCRIPTION

The present invention overcomes at least some of the aforementioned issues by providing a goggle accessory and goggle assembly that incorporate a goggle and the goggle accessory. More specifically, aspects of the present invention provide a goggle accessory for use with goggles and, optionally, a helmet that improves upon the current goggle aesthetic.

Therefore, according to one embodiment of the present invention, an accessory comprises a substantially planar element having at least one folding element along a longitudinal axis thereof, thereby dividing the substantially planar element into a plurality of substantially planar sections; an attachment means configured to attach the plurality of substantially planar sections to each other; and a plurality of openings through the substantially planar element configured to receive a goggle keeper-strap.

According to another embodiment of the present invention, an accessory for use in conjunction with a goggle and a helmet comprises a longitudinal, planar element, wherein the longitudinal, planar element is made of a flexible material; and an attachment means configured to attach the longitudinal planar element to a strap of the goggle, thereby further defining an opening for a goggle-keeper strap of the helmet to pass between the strap of the goggle and at least a portion of the longitudinal, planar element.

According to another embodiment of the present invention, an accessory for use with a goggle, the goggle comprises a lenswear assembly and a strap, the accessory comprises a longitudinal, flexible element; an attachment means on the longitudinal, flexible element, wherein the attachment means is configured to attach the longitudinal, flexible element to the strap; and, one of: a plurality of coaxial openings, through the longitudinal, flexible element; and an opening between the longitudinal, flexible element and the strap, defined by the attachment of the longitudinal, flexible element to the strap.

According to another embodiment of the present invention, an accessory for use with a goggle and a helmet, the goggle comprising a lenswear assembly and a strap, the helmet comprising a head-covering shell and a goggle-keeper strap, the accessory comprises a flexible backing element; a design element on an outer surface of or integrated with the flexible backing element; and a plurality of openings, through one of the flexible backing element and the design element, configured to receive the goggle-keeper strap therethrough, further wherein one of the flexible backing element and the design element is configured to attach to a portion of the strap.

Various other features and advantages of the present invention will be made apparent from the following detailed description and the drawings.

BRIEF DESCRIPTION OF THE DRAWINGS

The drawings illustrate one embodiment presently contemplated for carrying out the invention.

DETAILED DESCRIPTION

Aspects of the present invention provide an accessory for use with goggles. A goggle assembly that includes goggles and the accessory is also disclosed. The accessory can be used in conjunction with goggles or with goggles and a helmet in various embodiments.

Figure 1:
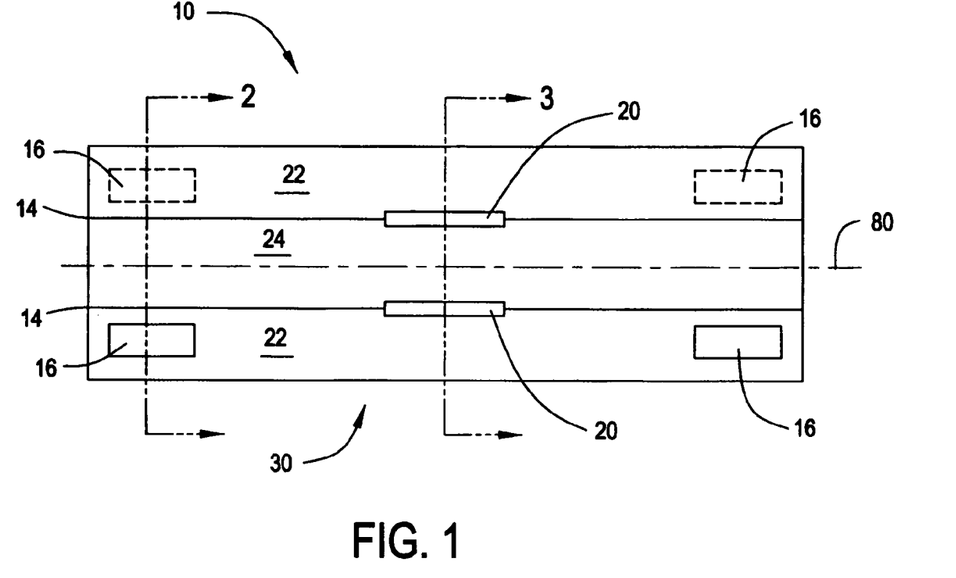
FIG. 1 is a front, elevation view of a goggle accessory, according to an embodiment of the present invention.

Referring to FIG. 1, a front, elevation view of a goggle accessory, according to an embodiment of the present invention, is shown. The accessory, depicted as element 10, includes a substantially planar element 30 that includes at least one folding element 14 along a longitudinal axis 80 of the substantially planar element 30. The at least one folding element 14 is configured so as to divide the substantially planar element 30 into a plurality of the substantially planar sections 22, 24. The accessory 10 further comprises an attachment means 16 that are configured to attach the plurality of substantially planar sections 22 to each other and/or the accessory directly to a strap of a goggle. The accessory 10 further comprises a plurality of openings 20 therethrough the substantially planar element 10 and configured to receive a goggle-keeper strap 74 (See e.g., FIGS. 5-10) of a helmet.

Figure 2:
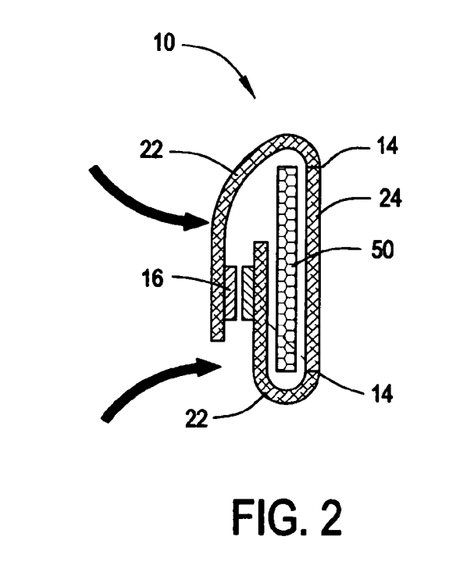
FIG. 2 is a side, elevation sectional view, along cut line 2-2 of FIG. 1, of the goggle accessory surrounding a goggle strap, according to an embodiment of the present invention.
Figure 3:
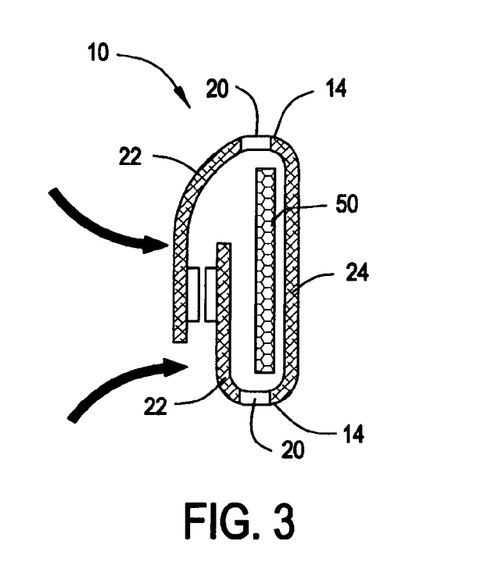
FIG. 3 is a side, elevation sectional view, along cut line 3-3 of FIG. 1, of the goggle accessory surrounding a goggle strap, according to an embodiment of the present invention.

Sectional cut lines 2-2 and 3-3 in FIG. 1 are for referring to the views depicted in FIGS. 2 and 3.

FIG. 2 shows a side, elevation sectional view, along cut line 2-2 of FIG. 1 (e.g., a distal end of the accessory 10), of the goggle accessory 10 surrounding a goggle strap 50, according to an embodiment of the present invention. As shown the movement arrows depict the movement of the two substantially planar sections 22 being folded at the folding elements 14 inwards towards the goggle strap 50 and the back of the center sections 24 such that the two substantially planar sections 22 may eventually be attached to each other via the attachment means 16. In this manner, the accessory 10 substantially surrounds a portion of the goggle strap 50.

Similarly, FIG. 3 shows a side, elevation sectional view, along cut line 3-3 of FIG. 1 (e.g., the center region of the goggle strap 50 and the accessory 10), of the goggle accessory 10 surrounding a goggle strap 50, according to an embodiment of the present invention. As shown, the accessory 10 substantially surrounds the goggle strap 50. The center region of the accessory 10 includes the plurality of openings 20 that are configured to receive the goggle keeper strap 74 (See e.g., FIGS. 5-11).

Referring generally to FIGS. 1-3, the attachment means 16 may comprise any suitable means to attach one portion of the accessory 10 to another. Suitable means comprise, for example, a snap, a hook and loop fastener, a button, a zipper, a pin clip, a magnet, a spring clip, combinations thereof, and the like. For example, the attachment means 16 shown in FIGS. 1-3 comprise a plurality of hook and loop fasteners located at peripheral regions of the accessory 10. Clearly, other locations and/or quantities of attachment means 16 than those depicted may be used without departing from aspects of the present invention. For example, the attachment means 16 may be located continually along the longitudinal length of the accessory 10.

Clearly, although FIGS. 1-3 depict two folding elements 14, other quantities and configuration of folding elements 14 may be used without departing from aspects of the present invention. For example, a single folding element 14 may be used wherein the folding element 14 divides the substantially planar element 30 into two substantially planar sections. The two or more substantially planar sections may or may not be of equal size. The folding element 14 may, for example, include one or more sewn seams, hems, sutures, or lines in the substantially planar element 30, if the substantially planar element 30 is made of a sewable material (e.g., cloth, leather, felt, etc.). If two or more folding elements 14 are used, they may be substantially parallel to each other. The folding elements 14 may be along the longitudinal axis 80. In an alternative embodiment, there may be no folding elements while at least portions of the accessory 10 are made of flexible material(s).

On, integrated to, and/or attached to an outer surface of the substantially planar element 30 may be one or more design elements 40 (See e.g., FIGS. 7-10). The design element 40 may comprise virtually any aesthetic design to distinguish and/or customize the accessory 10. For example, additional materials, items, designs may be used and attached to and/or integrated with the substantially planar element 30. Additionally, any logo, alphanumeric, artistic design, and the like may be part of the design element 40. In this manner, the design element(s) 40 can customize the accessory 10 and thereby to be viewed on the outer portion of the goggle band 50 and from the back of the helmet 70. In an embodiment, the design element 40 may be removably attachable to the accessory 10. In this manner, various design elements 40 may be changed and alternately attached to the accessory 10 resulting in numerous aesthetic looks to the accessory. Any suitable means may be used to removably attach the design element 40 to the accessory 10.

The attachment means 16 and at least one folding element 14 may be configured so as to substantially surround the substantially planar element 30 around a portion of the goggle strap 50, as depicted for example in FIGS. 2 and 3. In embodiments, portions of the length of the substantially planar element and/or substantially planar sections need not surround the goggle strap 50. For example, an embodiment may include a substantially planar element 30 that is a shape other than rectangular. In an embodiment the shape of the substantially planar element 30 may be, for example, H-shaped. In an embodiment the substantially planar element 30 may have extension portions in the area of the attachment means 16.

The substantially planar element 30 may comprise any suitable material, or combinations of materials. In an embodiment, at least a portion of the substantially planar element 30 is made of a flexible material. The flexible material may comprise any suitable material having suitable thickness, elasticity or combinations thereof to aid in the conforming of the accessory 10 to portions of a goggle strap 50 and, if used, a helmet 70 (See e.g., FIG. 5). Flexible materials used may be any suitable synthetic or natural materials or combinations thereof. The flexible material use may comprise cotton, cotton blend, fabric, canvas, rubber, plastic, nylon, fleece, corduroy, ribbon, leather, combinations thereof, and the like. The length (dimension along longitudinal axis) of the substantially planar element 30 may be any suitable length so as to attach to and/or surround a portion of a goggle strap. For example, the length may be in a range from about three inches to about 24 inches.

The plurality of openings 20 shown, for example in FIGS. 1 and 3, may be substantially coaxial and located in a center region, or portion, of the substantially planar element 30. The relative location of the plurality of openings 20 to each other and their location on the substantially planar element 30 are such to aid in providing openings and a path to guide and receive the goggle keeper strap 74 (FIG. 5) therethrough. Although in FIG. 1, the openings 20 are shown as rectangular, clearly other shapes and configurations are allowable without departing from the intent of the invention. Clearly, other locations, configurations, and quantities of openings 20 may be used without departing from aspects of the present invention. In another embodiment, there may be no openings on the substantially planar element 30. In such an embodiment a goggle-keeper strap 74 may pass entirely over (i.e., on the outside) of the accessory 10. In yet another embodiment, an opening may be defined between the goggle strap 50 and a portion of the accessory 10. In such an embodiment, the goggle-keeper strap 74 may pass under, therethrough, or entirely over (i.e., on the outside) of the accessory 10. In other embodiments, the accessory 10 may be used with a helmet that does not use a goggle-keeper strap 74. In still other embodiments, the accessory 10 may be used with goggles 60 but not with a helmet 70.

Figure 4:
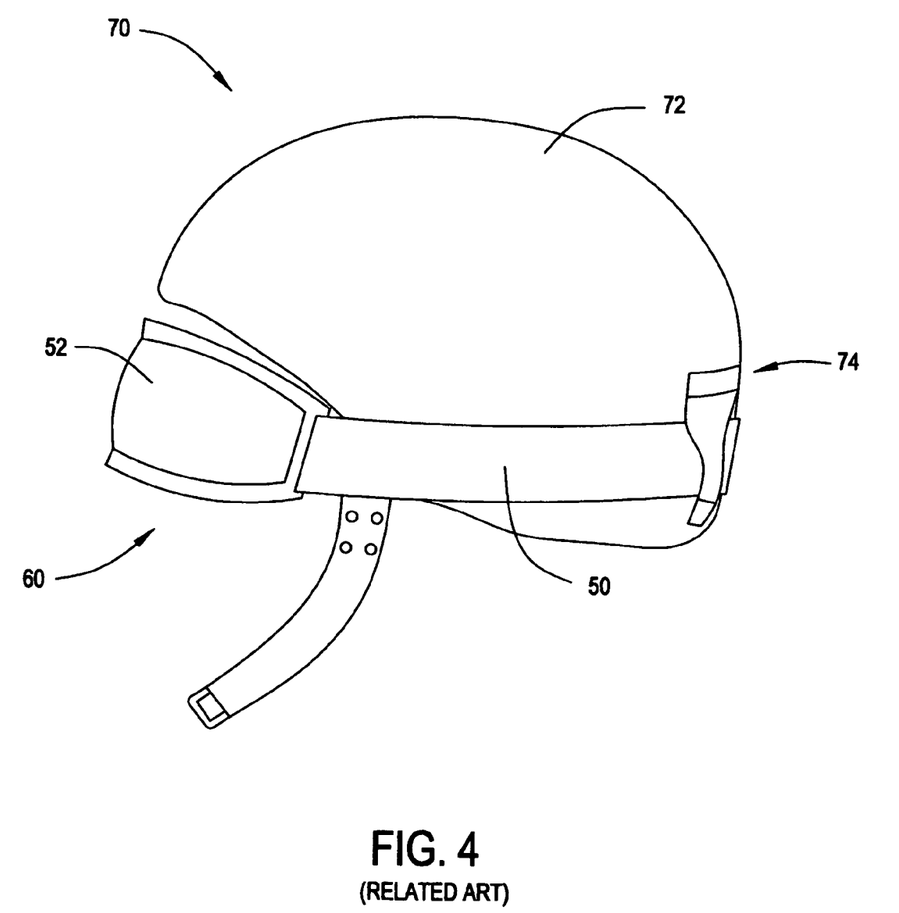
FIG. 4 is a side, perspective view of a helmet and a goggle of the related art.

FIG. 4 shows a side, perspective view of a helmet and a goggle of the related art. Aspects of the present invention may be employed in the environment depicted therein. As depicted, the helmet 70 includes an outer or head-covering shell 72 and chin strap. The helmet 70 further includes a goggle-keeper strap 74 on the rear portion of the helmet 70. Also shown is a goggle 60 that comprises an eyewear lens assembly, or eye-covering portion 52 and a goggle strap 50. The goggle strap 50 is attached to the eye-covering portion 52 and is configured to attach the eye-covering portion 52 to a head of a user (not shown) so that the eye-covering portion 52 is over the eyes of the user. A portion of the goggle-keeper strap 74 is removably attached to the head-covering shell 72 of the helmet 70. As shown, the goggle-keeper strap 74 attaches over a center portion of the goggle strap 50 so as to keep the goggle strap 50 from riding upwards, or downwards, along the shell 72 and thereby causing the eye-covering portion 52 of the goggles 60 to become displaced from the user's eyes and face.

Figure 5:
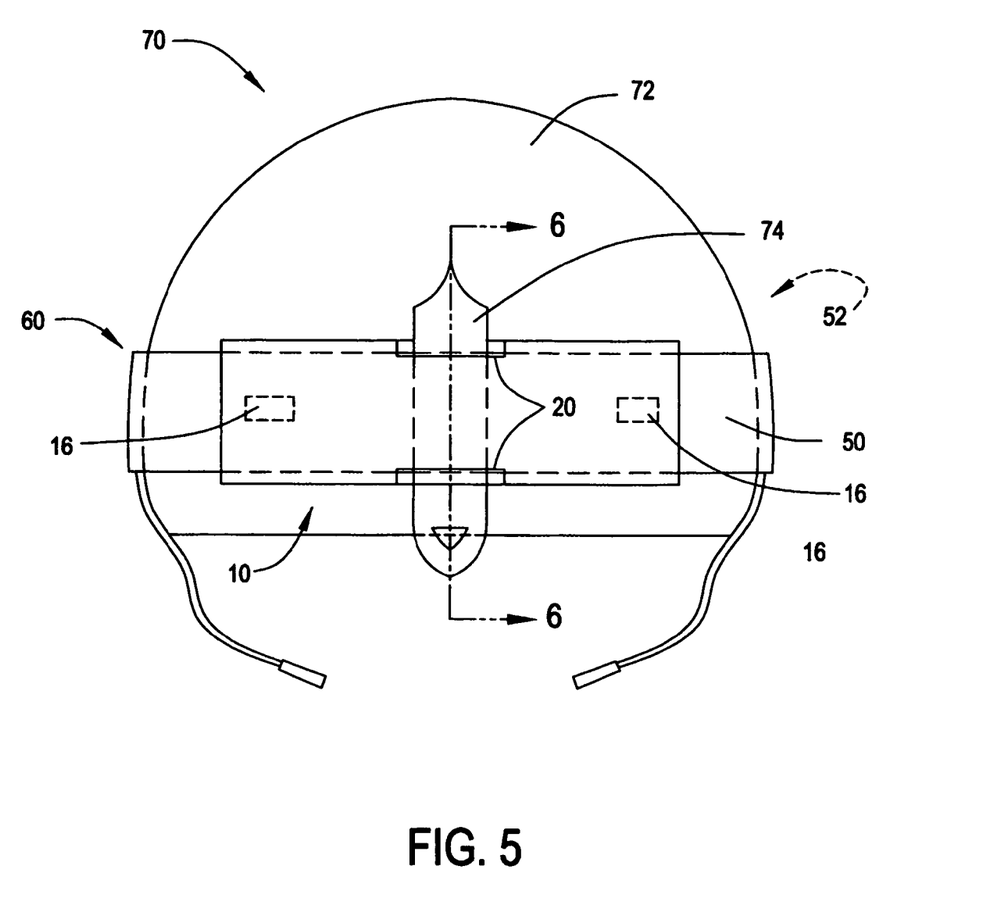
FIG. 5 is a rear, elevation view of a helmet with a goggle assembly attached thereto, according to an embodiment of the present invention.

Referring now to FIG. 5 a rear, elevation view of a helmet with a goggle assembly attached thereto is shown, according to an embodiment of the present invention. As shown, a helmet 70 having a helmet shell 72 has a goggle 60 attached thereto. The goggle 60 includes an eye covering portion 52 and a goggle strap 50. The goggle accessory 10 is attached to and/or substantially surrounding a portion of the goggle strap 50. In this manner the decorative aspect of the goggle accessory 10 is viewable from the back of the user in lieu of viewing portions of the goggle strap 50. The goggle-keeper strap 74 is in use on the back of the helmet 70 such that the goggle-keeper strap 74 is leafed through the openings 20 of the accessory 10 such that a portion of the goggle-keeper strap 74 is covering a portion of the goggle strap 50 but hid from view behind a portion of the goggle accessory 10.

Figure 6:
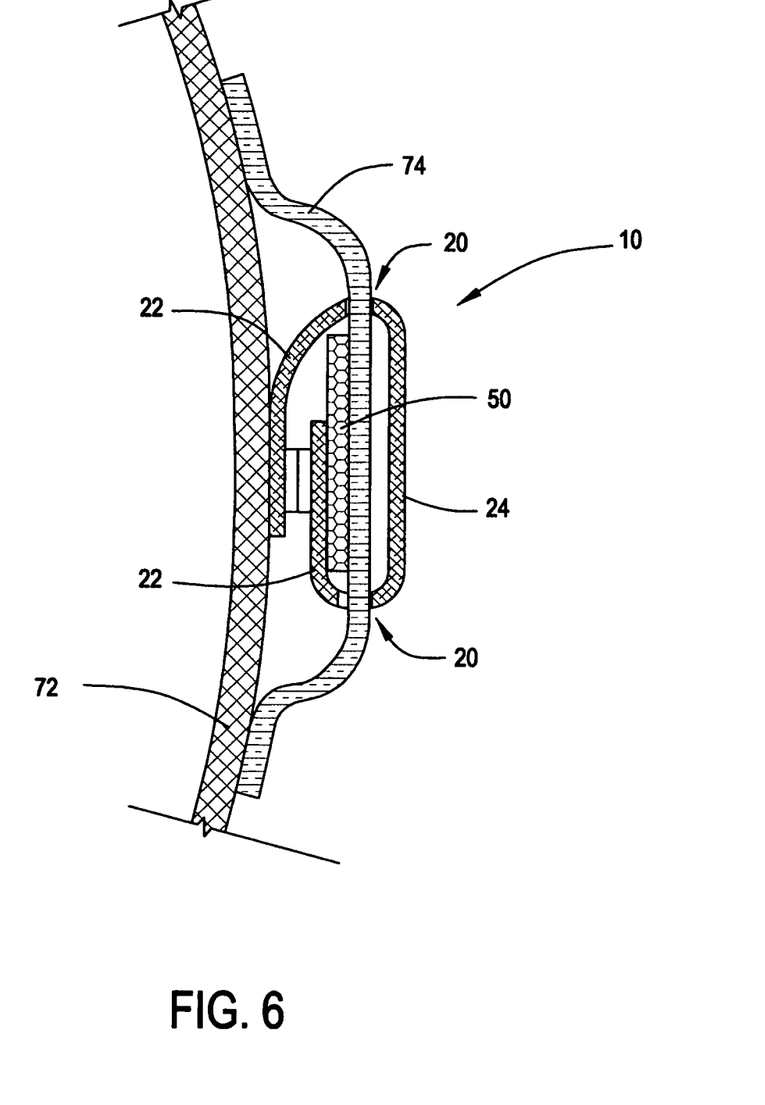
FIG. 6 is a side, elevation sectional view, along cut line 6-6 of FIG. 5, of the helmet, the goggle strap, and goggle accessory, according to an embodiment of the present invention.

FIG. 6 shows a close-up, side, elevation sectional view, along cut line 6-6 of FIG. 5, of the helmet 70, the goggle strap 50, and goggle accessory 10, according to an embodiment of the present invention. As shown, the goggle-keeper strap 74 of the helmet 70 is received through the openings 20 of the accessory 10. The substantially planar sections 22 and the center section 24 of the accessory 10 substantially surrounds the goggle strap 50. The distal ends of the goggle-keeper strap 74 are attached to the shell 72 of the helmet 70. In this manner, the goggle-keeper strap 74 function of being able to keep the goggle strap 50 from riding upwards, or downwards, on the helmet shell 72 is maintained while concomitantly the aesthetic aspects of the goggle accessory 10 is able to be viewed and enjoyed.

FIGS. 7-10 depict multiple side, elevation sectional views, taken along a center portion of the goggle assembly, of a goggle strap, goggle-keeper strap, and goggle accessory, according to various embodiments of the present invention. The goggle strap 50 and the means by which the goggle accessory 10 is attached to and/or surround the goggle strap 50 are not shown for clarity purposes only. In the figures the accessory 10 includes a backing element 45 and a design element 40. Clearly, other embodiments may not include a separate design element 40 from the backing element 45 without departing from aspects of the present invention.

Figures 7, 8:
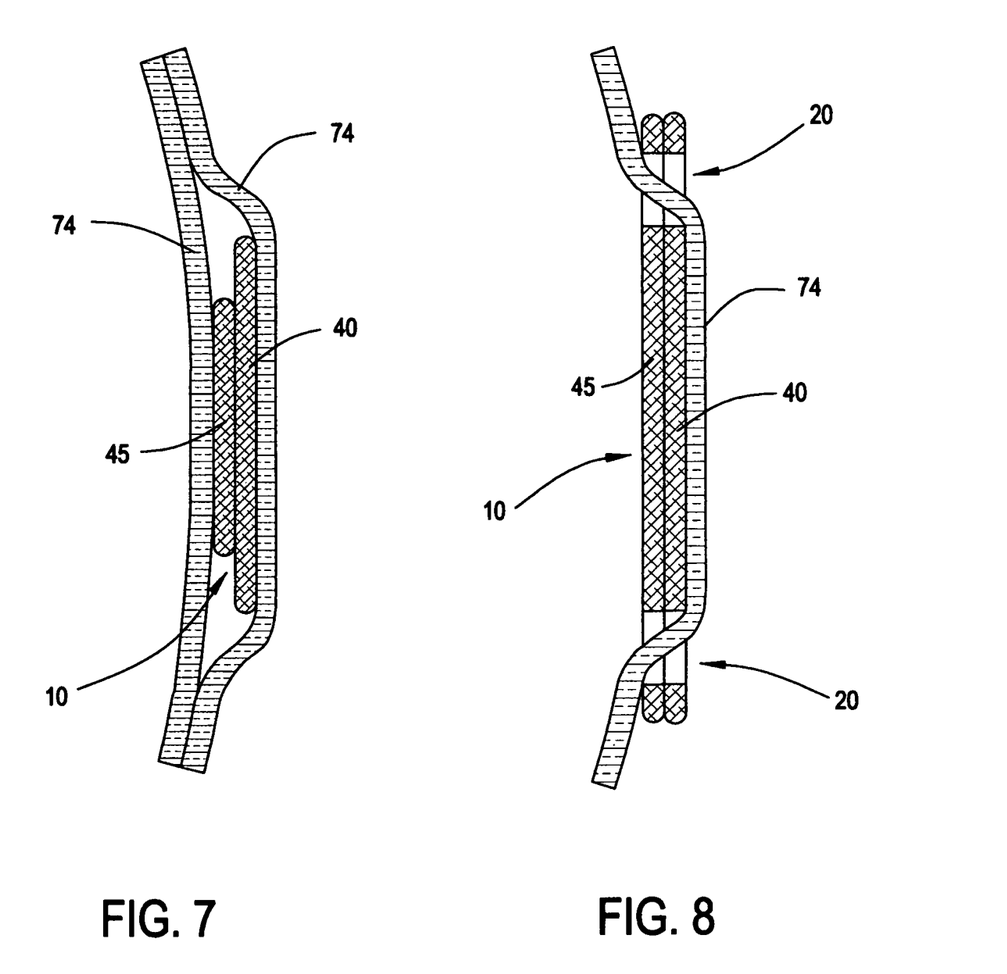
FIGS. 7-10 are side, elevation sectional views, taken along a center portion of the goggle assembly, of a goggle strap, goggle-keeper strap, and goggle accessory, according to various embodiments of the present invention.
Figure 9:
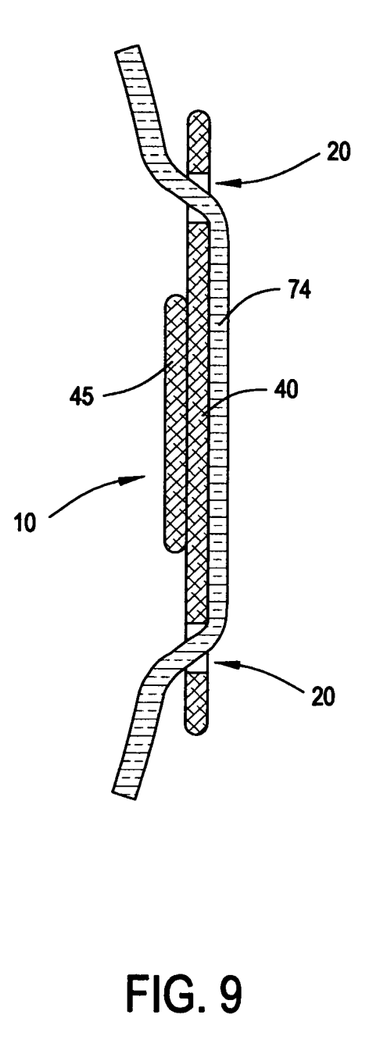
Figure 10:
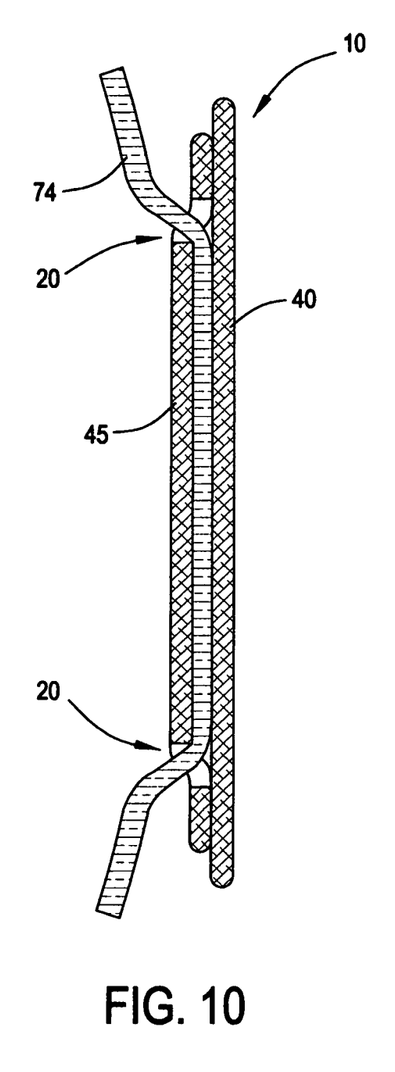

For example, FIG. 7 depicts two variations of the interaction of the goggle-keeper strap 74 and the goggle accessory 10. As shown, in an embodiment, the goggle-keeper strap 74 may be behind the entire goggle accessory 10 (i.e., behind both the backing element 45 and the design element 40). In another embodiment the goggle-keeper strap 74 may be placed over the entire goggle accessory 10 (i.e., over both the backing element 45 and the design element 40).

In FIG. 8 the goggle-keeper strap 74 is guided through the openings 20 that are through both the backing element 45 and the design element 40 of the goggle accessory 10. Contrastingly, in FIG. 9 the goggle-keeper strap 74 is guided through the openings 20 that are only on the design element 40 of the goggle accessory 10. In the embodiment shown in FIG. 10, the goggle-keeper strap 74 is guided through the openings 20 that are only through the backing element 45 of the goggle accessory 10. In this embodiment, the goggle-keeper strap 74 is guided through an opening, or path, between the backing element 45 and the design element 40. In this manner the goggle-keeper strap 74 may, or may not (depending on the embodiment in the various figures), be seen on the over the goggle accessory 10.

In another embodiment various other accessories or elements may be integrated and/or attached to the goggle accessory 10. For example, other devices may be integrated and/or attached such as a reservoir, pocket, holder element, or combinations thereof (not shown). The reservoir may be used to contain liquids or semi-liquids such as, for example, goggle lens cleaner, goggle defogger, lip balm, and the like. The pocket may be suitable for containing money, identification cards (e.g., ski lift pass), credit cards, electronics and the like. The holder element (e.g., spring clip, slot, magnet, etc.) may provide for the removable attachment of items such as makeup, lip balm, electronics, cameras, and the like. In this manner, functions beyond merely aesthetic improvement of the goggle strap 50 may be provided.

Therefore, according to one embodiment of the present invention, an accessory comprises a substantially planar element having at least one folding element along a longitudinal axis thereof, thereby dividing the substantially planar element into a plurality of substantially planar sections; an attachment means configured to attach the plurality of substantially planar sections to each other; and a plurality of openings through the substantially planar element configured to receive a goggle keeper-strap.

According to another embodiment of the present invention, an accessory for use in conjunction with a goggle and a helmet comprises a longitudinal, planar element, wherein the longitudinal, planar element is made of a flexible material; and an attachment means configured to attach the longitudinal planar element to a strap of the goggle, thereby further defining an opening for a goggle-keeper strap of the helmet to pass between the strap of the goggle and at least a portion of the longitudinal, planar element.

According to another embodiment of the present invention, an accessory for use with a goggle, the goggle comprises a lenswear assembly and a strap, the accessory comprises a longitudinal, flexible element; an attachment means on the longitudinal, flexible element, wherein the attachment means is configured to attach the longitudinal, flexible element to the strap; and, one of: a plurality of coaxial openings, through the longitudinal, flexible element; and an opening between the longitudinal, flexible element and the strap, defined by the attachment of the longitudinal, flexible element to the strap.

According to another embodiment of the present invention, an accessory for use with a goggle and a helmet, the goggle comprising a lenswear assembly and a strap, the helmet comprising a head-covering shell and a goggle-keeper strap, the accessory comprises a flexible backing element; a design element on an outer surface of or integrated with the flexible backing element; and a plurality of openings, through one of the flexible backing element and the design element, configured to receive the goggle-keeper strap therethrough, further wherein one of the flexible backing element and the design element is configured to attach to a portion of the strap.

The present invention has been described in terms of the preferred embodiment, and it is recognized that equivalents, alternatives, and modifications, aside from those expressly stated, are possible and within the scope of the appending claims.

What is claimed is:

1. A goggle accessory comprising:
   a substantially planar element having first and second folding elements parallel to a longitudinal axis, wherein the first and second folding elements define a center portion of the goggle accessory and wherein each of the first and second folding elements comprises at least one of a sewn seam, hem, suture, or line in the substantially planar element, wherein the first and second folding elements are substantially straight lines that are parallel to each other and wherein the at least one of sewn seam, hem, suture, or line in the substantially planar element is parallel to the longitudinal axis;
   an entry opening through the first folding element; and
   an exit opening through the second folding element, wherein the entry opening and exit opening are parallel to the longitudinal axis.

2. The goggle accessory of claim 1 further comprising a fastener that includes at least one of a snap, a hook and loop fastener, a button, a zipper, a pin clip, a magnet, and a spring clip.

3. A helmet accessory comprising:
   an outer surface comprising a substantially planar element;
   a first substantially planar distal portion coupled to the outer surface by a first folding element, wherein the first folding element comprises a substantially straight line formed by a sewn seam;
   a second substantially planar distal portion coupled to the outer surface by a second folding element and coupled to the first distal portion by a fastener, wherein the second folding element comprises a substantially straight line formed by a sewn seam;
   a surrounding for a goggle strap at least partly defined by the outer surface, the first substantially planar distal portion, and the second substantially planar distal portion, the surrounding for a goggle strap running along a longitudinal axis parallel to the first folding element and second folding element; and
   a first opening passing through the first folding element and a second opening passing through the second folding element, the first and second openings located at a center portion of the surrounding for a goggle strap along the longitudinal axis.

4. The helmet accessory of claim 3 further comprising a path at least partly defined by the outer surface, the first substantially planar distal portion, and the second substantially planar distal portion, the path running along an axis perpendicular to the longitudinal axis.

5. The helmet accessory of claim 4, wherein the path comprises an entry at the first opening and an exit at the second opening.

6. A goggle keeper helmet accessory comprising:
   a substantially planar element (30) having a rectangular shape, the substantially planar element comprising:
      a first substantially planar section (22) having a rectangular shape, the first substantially planar section comprising:
         a first attachment means (16) comprising at least one of a snap, a hook and loop fastener, a button, a zipper, a pin clip, a magnet, and a spring clip; and
         a second attachment means (16) comprising at least one of a snap, a hook and loop fastener, a button, a zipper, a pin clip, a magnet, and a spring clip,
         wherein the first attachment means and the second attachment means are coupled to an inner surface of the substantially planar element;
      a center section (24) having a rectangular shape;
      a second substantially planar section (22) having a rectangular shape, the second substantially planar section comprising:
         a third attachment means (16) comprising at least one of a snap, a hook and loop fastener, a button, a zipper, a pin clip, a magnet, and a spring clip, the third attachment means complementary with the first attachment means; and
         a fourth attachment means (16) comprising at least one of a snap, a hook and loop fastener, a button, a zipper, a pin clip, a magnet, and a spring clip, the fourth attachment means complementary with the second attachment means;
         wherein the third attachment means and the fourth attachment means are coupled to an outer surface of the substantially planar element;
      a first folding element (14) along a longitudinal axis (80) that defines a boundary between the first substantially planar section and the center section;
      a second folding element (14) along a longitudinal axis (80) that defines a boundary between the center section and the second substantially planar section;
      a first opening (20) through the substantially planar element at a center position along the first folding element;
      a second opening (20) through the substantially planar element at a center position along the second folding element, wherein the first opening and second opening are substantially coaxial; and
      a design element (40) along the outer surface of the substantially planar element at the center section,
   wherein, when the substantially planar element is folded along the first folding element and folded along the second folding element and when the first attachment means is coupled to the third attachment means and the second attachment means is coupled to the fourth attachment means:
      the substantially planar element is able to surround, at the inner surface of the substantially planar element, a portion of a goggle strap running along the longitudinal axis, and
      the substantially planar element is able to allow a goggle keeper strap to pass through the first opening and the second opening such that a portion of the goggle keeper strap is surrounded by the substantially planar element at the inner surface of the substantially planar element, the goggle keeper strap running along an axis that is perpendicular to the longitudinal axis.

* * * * *